United States Patent
Yang et al.

(10) Patent No.: US 9,690,035 B2
(45) Date of Patent: Jun. 27, 2017

(54) FUNCTIONAL MATERIAL, ITS PREPARATION METHOD, LIGHT GUIDE INK, AND LIGHT GUIDE PLATE

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jiuxia Yang, Beijing (CN); Feng Bai, Beijing (CN); Jiantao Liu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 14/771,040

(22) PCT Filed: Nov. 21, 2014

(86) PCT No.: PCT/CN2014/091859
§ 371 (c)(1),
(2) Date: Aug. 27, 2015

(87) PCT Pub. No.: WO2016/015412
PCT Pub. Date: Feb. 4, 2016

(65) Prior Publication Data
US 2016/0370531 A1    Dec. 22, 2016

(30) Foreign Application Priority Data
Jul. 29, 2014   (CN) .......................... 2014 1 0367169

(51) Int. Cl.
*F21V 8/00* (2006.01)
*C09K 11/02* (2006.01)
(Continued)

(52) U.S. Cl.
CPC ............ *G02B 6/0043* (2013.01); *A61K 41/00* (2013.01); *C09C 1/0081* (2013.01);
(Continued)

(58) Field of Classification Search
CPC ...... G02B 6/0043; C09D 11/50; C09K 11/025
See application file for complete search history.

(56) References Cited

U.S. PATENT DOCUMENTS 4,360,626 A   11/1982  Manwiller
4,759,987 A   7/1988   Mizobe et al.
(Continued)

FOREIGN PATENT DOCUMENTS

CN   1201046 A   12/1998
CN   1653147 A   8/2005
(Continued)

OTHER PUBLICATIONS

International Search Report and Written Opinion mailed May 4, 2015; PCT/CN2014/091859.
(Continued)

*Primary Examiner* — Elmito Breval
(74) *Attorney, Agent, or Firm* — Ladas & Parry LLP

(57) ABSTRACT

The present invention provides a functional material, its preparation method, a light guide ink and a light guide plate. The present invention belongs to the display technical field and can solve the problem that existing liquid crystal display devices will produce pollution. The functional material of the present invention includes an inorganic powder whose surface has a modified layer, wherein the inorganic powder includes any one or more of aluminum oxide, magnesium
(Continued)

oxide, zinc oxide, zirconium oxide, silicon dioxide, titanium dioxide, boron oxide, diiron trioxide, calcium oxide, potassium oxide, sodium oxide and lithium oxide; and the modified layer is generated by a reaction of a dianhydride and a diamine. The light guide ink of the present invention includes the above functional material. The light guide plate of the present invention includes a scattering pattern formed by curing the above light guide ink.

8 Claims, 1 Drawing Sheet

(51) Int. Cl.
*C09C 3/10* (2006.01)
*A61K 41/00* (2006.01)
*C09C 1/00* (2006.01)
*C09D 11/107* (2014.01)
*C09D 11/50* (2014.01)
*C09K 11/67* (2006.01)

(52) U.S. Cl.
CPC ............ *C09C 1/0084* (2013.01); *C09C 3/10* (2013.01); *C09D 11/107* (2013.01); *C09D 11/50* (2013.01); *C09K 11/025* (2013.01); *C09K 11/676* (2013.01); *C09K 11/678* (2013.01); *G02B 6/0065* (2013.01)

(56) References Cited

U.S. PATENT DOCUMENTS

| 6,146,762 A | 11/2000 | D'Herbecourt et al. |
| 2005/0164002 A1 | 7/2005 | Krizan et al. |
| 2011/0123722 A1 | 5/2011 | Yang et al. |
| 2013/0037786 A1* | 2/2013 | Miyao ................. C08K 9/04 257/40 |

FOREIGN PATENT DOCUMENTS

| CN | 101407620 A | 4/2009 |
| CN | 101805517 A | 8/2010 |
| CN | 101831175 A | 9/2010 |
| CN | 102079899 A | 6/2011 |
| CN | 102140230 A | 8/2011 |
| CN | 103555003 A | 2/2014 |
| EP | 1912084 A1 | 4/2008 |
| JP | 2002-062537 A | 2/2002 |

OTHER PUBLICATIONS

First Chinese Office Action dated Jun. 10, 2015; Appln. No. 201410367169.0

Notice of Allowance Appln. No. 201410367169.0; Dated Feb. 26, 2016.

* cited by examiner

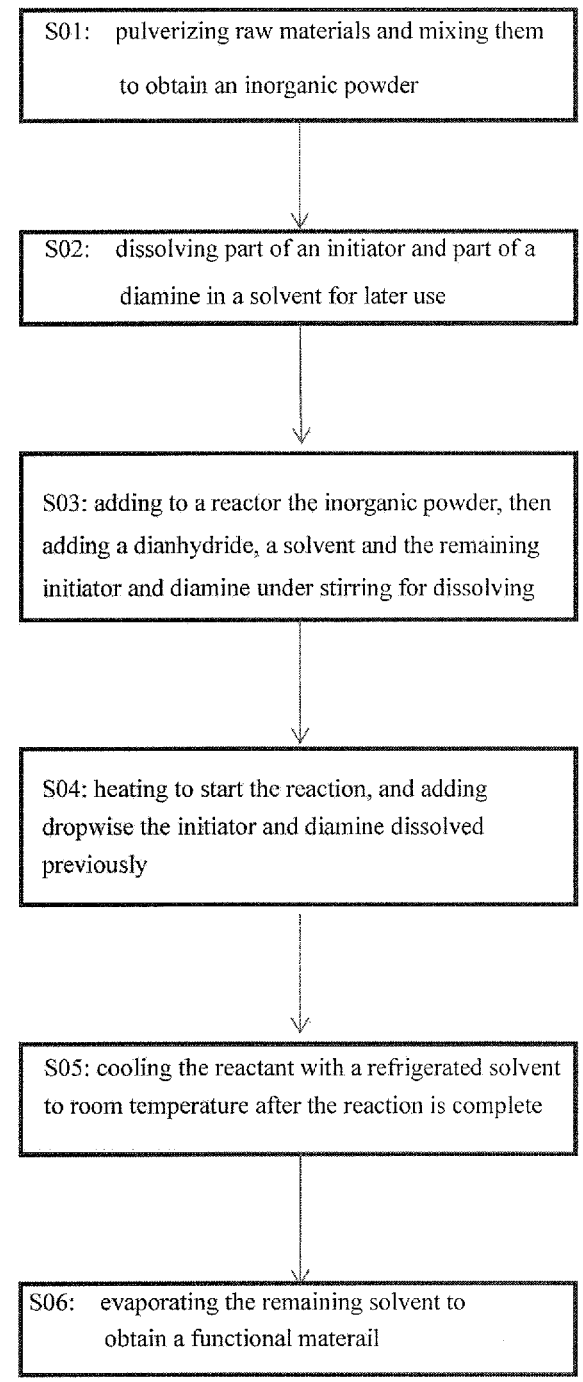

FUNCTIONAL MATERIAL, ITS PREPARATION METHOD, LIGHT GUIDE INK, AND LIGHT GUIDE PLATE

TECHNICAL FIELD

The present invention relates to the display technical field, in particular to a functional material, its preparation method, a light guide ink and a light guide plate.

BACKGROUND

A light guide plate is an important component in a liquid crystal display device and has a light-exiting surface and a back surface opposite to the light-exiting surface, wherein a scattering pattern (for example, a scattering network) may be provided on the back surface of the light guide plate, the scattering pattern allowing the light provided thereon to be scattered and emitted from the light-exiting surface for use in a liquid crystal panel. The above scattering pattern can be formed by curing a light guide ink. In another word, the light guide ink can be applied onto a predetermined region of the back surface of a light guide plate and then be cured to form a scattering pattern, wherein the light guide ink typically comprises a curable resin, a scattering particle, an initiator, a solvent, a pigment, an additive and the like.

Liquid crystal display devices will inevitably produce some electromagnetic radiation during use, resulting in adverse effects on human health.

SUMMARY OF THE INVENTION

Regarding the problem that existing liquid crystal display devices will produce pollution, the present invention provides an environmentally friendly functional material which may play a role in health care and a method for preparing the same, as well as a light guide ink and a light guide plate.

One technical solution employed to solve a technical problem of the present invention is a functional material comprising an inorganic powder whose surface has a modified layer, wherein the inorganic powder comprises any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; and the modified layer is generated by a reaction of a dianhydride and a diamine.

For example, the molar ratio of the dianhydride to the diamine for generating the modified layer is from 0.85:1 to 1.05:1.

Further preferably, the molar ratio of the dianhydride to the diamine for generating the modified layer is from 0.92:1 to 1.05:1.

For example, the dianhydride for generating the modified layer comprises at least one phenyl group, and the diamine for generating the modified layer comprises at least one phenyl ring or at least one non-phenyl six-membered carbocyclic ring.

Further preferably, the dianhydride for generating the modified layer is selected from any one of pyromellitic dianhydride, trimellitic anhydride, benzophenone dianhydride, biphenyl dianhydride, diphenyl ether dianhydride, and 4,4'-(hexafluoroisopropylidene) diphthalic anhydride (also named as Hexafluoro Dianhydride); and the diamine for generating the modified layer is selected from any one of 3-amino benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl] hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-di-aminofluorene, m-xylylenediamine, and 4,4'-methylene bis (2-ethyl-6-methylaniline).

For example, the inorganic powder has a particle diameter of 1 to 5000 nm.

One technical solution employed to solve a technical problem of the present invention is a method for preparing the above functional material, comprising: mixing the inorganic powder, the dianhydride, and the diamine with an initiator and a solvent uniformly; and reacting the dianhydride with the diamine by heating to form the modified layer on the surface of the inorganic powder.

For example, the mass ratio of the inorganic powder to the substance generated by the reaction of the dianhydride and the diamine is from 20:1 to 1:1.

For example, the heating comprises two stages, specifically: heating at a temperature of 35° C. to 70° C. for 20 to 40 min; and heating at a temperature of 70° C. to 100° C. for 20 to 40 min.

One technical solution employed to solve a technical problem of the present invention is a light guide ink comprising: a curable resin; a scattering particle; a solvent; and the above functional material.

For example, the light guide ink further comprises a pigment, an additive and an initiator; and without calculating the mass of the modified layer in the functional material, the mass percentages of the components in the light guide ink are: the scattering particle: 2 to 25%; the curable resin: 10 to 50%; the pigment: 0.01 to 0.5%; the solvent: 20 to 75%; and the initiator: 0 to 8.5%.

For example, without calculating the mass of the modified layer in the functional material, the mass percentage of the inorganic powder in the functional material is 0.1 to 2.5% based on the light guide ink.

Preferably, without calculating the mass of the modified layer in the functional material, the mass percentage of the inorganic powder in the functional material is 0.1 to 2% based on the light guide ink.

More preferably, without calculating the mass of the modified layer in the functional material, the mass percentage of the inorganic powder in the functional material is 0.1 to 1.8% based on the light guide ink.

The expression "without calculating the mass of the modified layer in the functional material, the mass percentage of a certain substance in the light guide ink" herein refers to the content of the certain substance in the case that the total mass of all substances in the light guide ink (the inorganic powder in the functional material, the scattering particle, the curable resin, the pigment, the solvent, the initiator and the like) except the modified layer in the functional material is 100%.

One technical solution employed to solve a technical problem of the present invention is a light guide plate, comprising a light-exiting surface and a back surface opposite to the light-exiting surface, wherein the back surface is provided with a scattering pattern formed by curing the above light guide ink.

The functional material of the present invention can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The surface of the inorganic powder in the functional material of the present invention has a modified layer which can allow the inorganic powder to be well incorporated into a light guide ink and can improve the inorganic powder's capacity to emit far-infrared light and negative ions.

The light guide plate of the present invention comprises a scattering pattern formed from the above light guide ink, and therefore can constantly emit far-infrared light and negative ions during use and is environmentally friendly.

BRIEF DESCRIPTION OF THE DRAWING

FIG. 1 is a flow chart of the method for preparing the functional material according to one embodiment of the present invention.

DETAILED DESCRIPTION

To enable those skilled in the art to better understand the technical solution of the present invention, further detailed descriptions are made for the present invention with reference to the drawing and embodiments.

The present embodiment provides a functional material and a method for preparing the same.

The functional material comprises an inorganic powder whose surface has a modified layer, wherein the inorganic powder comprises any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; and the modified layer is generated by a reaction of a dianhydride and a diamine.

The particle diameter of the inorganic powder is from nanometers to micrometers, specifically, e.g., 1 to 5000 nm, preferably 10 to 500 nm. The particle diameter may be measured for example by a Malvern laser particle size analyzer.

Dianhydride refers to a substance containing at least two anhydride groups in the molecular structure, and diamine refers to a substance containing at least two amine groups (or amino groups) in the molecular structure.

The dianhydride, for example, contains at least one phenyl group, and is preferably any one of pyromellitic dianhydride, trimellitic anhydride, benzophenone dianhydride, biphenyl dianhydride, diphenyl ether dianhydride, and 4,4'-(hexafluoroisopropylidene) diphthalic anhydride (also named as hexafluoro dianhydride).

The diamine, for example, contains at least one phenyl ring or at least one non-phenyl six-membered carbocyclic ring (e.g. cyclohexyl), and is preferably any one of 3-amino benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl] hexafluoropropane, 2,2-bis(3-amino-4-methylphenyl) hexafluoropropane, 2,2-bis(3-aminophenyl) hexafluoropropane, 2,2- bis(4-aminophenyl) hexafluoropropane, 2,7-diamino fluorene, m-xylylene diamine, and 4,4'-methylene bis(2-ethyl-6-methylaniline).

The molar ratio of the dianhydride to the diamine is from 0.85:1 to 1.05:1, preferably from 0.92:1 to 1.05:1.

Our study has revealed that the modified layer generated by the reaction of the above dianhydride and diamine can desirably improve the properties of the inorganic powder.

The functional material of the present embodiment can emit far-infrared light and negative ions. Far-infrared light, after being absorbed by a human body, can allow water molecules in the body to resonate and be activated, which enhances the intermolecular bonding force, thereby activating proteins and other biological macromolecules and bringing the organism cells to the highest vibration level. Furthermore, far-infrared heat can be transferred to a subcutaneous deeper part, thus increasing the temperature of the subcutaneous deeper part, expanding the capillaries, promoting the blood circulation, strengthening the metabolism among tissues, promoting a tissue regeneration capacity, enhancing the organism immunity, and bringing the vivacity. On the other hand, negative ions can decompose and oxidize bacteria and organic substances, and may serve the function of disinfection and sterilization and produce the effect of improving air quality. Therefore, the functional material may play a role in health care and is environmentally friendly.

The method for preparing the above functional material comprises: mixing the inorganic powder, the dianhydride, and the diamine with an initiator and a solvent uniformly; and reacting the dianhydride with the diamine by heating to form the modified layer on the surface of the inorganic powder.

Specifically, as shown in FIG. 1, the above preparation method may comprise:

S01, in the case of using a dispersant, pulverizing various materials into powder respectively and then uniformly mixing them proportionally, or uniformly mixing various materials proportionally and then pulverizing them, to yield an inorganic powder.

The dispersant may be chosen from conventional dispersants such as BYK 161 manufactured by BYK Additives & Instruments and Solsperse 32500 and Solsperse 22000 manufactured by The Lubrizol Corporation. Pulverization may be carried out using conventional methods such as ball milling, grinding, and the like. As the inorganic powder may be prepared by existing methods, no further details will be provided herein.

S02, dissolving from a fourth to a third of an initiator and from a fourth to a third of a diamine in a solvent for later use.

The mass ratio of the inorganic powder to the substance generated by the reaction of the dianhydride and the diamine is from 20:1 to 1:1.

That is to say, the amounts of the dianhydride and the diamine are determined according to the following manner: assuming a complete reaction between the dianhydride and the diamine to yield a resultant (which is actually a modified layer), if the mass of the resultant is 1, then the mass of the inorganic powder will be between 1 and 20. Such an amount can ensure that a modifier layer with a suitable thickness can be obtained on the inorganic powder.

An initiator is used to initiate the reaction, which, for example, is a nitrogen-based initiator, and is preferably any one of azo bisisobutyronitrile, 2,2'-azo bis(2,4-dimethylvaleronitrile), dimethyl azo bisisobutyrate, and azo bisisovaleronitrile.

The solvent can be selected from fatty alcohols, glycol ethers, ethyl acetate, methyl ethyl ketone, methyl isobutyl ketone, ethylene glycol monomethyl ether ester, γ-butyrolactone, ethyl 3-ethoxypropionate, butyl carbitol, butyl carbitol acetate, propylene glycol monomethyl ether, propylene glycol monomethyl ether acetate, cyclohexane, xylene, isopropanol, and other conventional organic solvents. Since the solvent merely serves to disperse various substances, propylene glycol monomethyl ether acetate is used as the solvent in the process of specifically preparing the functional material in all the Examples.

S03, adding the inorganic powder to a reaction vessel (e.g., a four-neck flask) which is then subjected to stirring, shocking, shaking and the like; afterwards, adding the dianhydride and the solvent as well as the remaining initiator and diamine and allowing them to be dissolved uniformly.

S04, heating to carry out the reaction, preferably in two stages, specifically comprising: heating at a temperature of 35° C. to 70° C. for 20 to 40 min; and then continuing heating at a temperature of 70 to 100° C. for 20 to 40 min.

During the above heating process, the dianhydride and the diamine are allowed to react, thereby generating a modified layer on the surface of the inorganic powder; wherein heating is carried out in two stages so as to prevent the reaction from being too severe.

During the reaction process, the above solution prepared by dissolving an initiator and a diamine is gradually added dropwise to a four-neck flask so as to prevent the reaction from being too severe.

The reaction in this step may be carried out, for example, under the protection of nitrogen, and for example under constant stirring.

The solvent in each step is in an amount sufficient to disperse and dissolve the substances therein uniformly, and the initiator is in an amount sufficient to initiate the reaction. These amounts can be adjusted by those skilled in the art according to the actual conditions, and thus no further detail is given herein. However, generally speaking, the mass ratio (referring to the total amount) of the inorganic powder, the initiator and the solvent is 1:(0.25 to 0.4):(1 to 1.5). To achieve consistency in the process of preparing the functional material in the various Examples, the mass ratio of the inorganic powder, the initiator and the solvent is 1:0.3:1.4.

S05, cooling the reactant with a refrigerated solvent to room temperature (about 10 to 30° C.) after the reaction is over.

S06, evaporating the remaining solvent or separating the powder therefrom to yield an inorganic powder with a modified layer, i.e., a functional material.

Of course, it should be appreciated that the preparation method described above may also undergo many changes, for example, the dianhydride, the diamine, the initiator and the like can all be dissolved in a solvent once; for another example, heating can be carried out at only one stage. After all, any variation is allowed as long as the dianhydride and the diamine can react to form a modified layer on the surface of the inorganic powder.

The present embodiment further provides a light guide ink.

The light guide ink is used for forming a scattering pattern on a light guide plate and comprises a curable resin, a scattering particle, a solvent and the above functional material. For example, the light guide ink may further comprise a pigment, an additive and an initiator.

For example, without calculating the mass of the modified layer in the functional material, the mass percentages of the components in the light guide ink are:
the functional material: 0.1 to 2.5%;
the scattering particle: 2 to 25%;
the curable resin: 10 to 50%;
the pigment: 0.01 to 0.5%;
the solvent: 20 to 75%; and
the initiator: 0 to 8.5%.

Without calculating the mass of the modified layer in the functional material, the mass percentage of the inorganic powder in the functional material is preferably 0.1 to 2%, more preferably 0.1 to 1.8% based on the light guide ink.

That is to say, the contents of the components are as above in the case that the total mass of all substances in the light guide ink (the inorganic powder in the functional material, the scattering particle, the curable resin, the pigment, the solvent, and the initiator) except the modified layer in the functional material is 100%.

A curable resin refers to a resin material that can be cured to form a solid film layer which can be well incorporated into a light guide plate for curing scattering particles, functional materials and the like therein to form a scattering pattern. For example, the curable resin may be a resin of vinyl unsaturated monomers (e.g. acrylate resins, polyurethane acrylates, epoxy acrylate resin, etc.), an epoxy resin, a thermosetting resin, a thermoplastic resin or the like.

The curable resin may be thermosetting or UV cured. For thermosetting resins, they are cured at a temperature from 50 to 80° C. because the light guide plate material is typically polymethyl methacrylate (PMMA) with a heat resistance at about 90° C. To ensure that the light guide plate is not damaged upon curing a light guide ink, the resin must be cured at a temperature below 90° C.

The scattering particles are used for scattering incident light to achieve the basic function of the scattering pattern and can be any one or more of titanium dioxide, barium sulfate, magnesium oxide, silicon oxide, zinc oxide, lithopone, and zirconium oxide; and the particle diameter is, for example, from 40 to 400 nm.

The solvent is used for dissolving and dispersing the various components in the light guide ink to form a uniform and stable system. The solvent can be selected from: acidic solvents such as formic acid, acetic acid, chloroform and the like; basic solvents such as ketones, esters, ethers and the like; neutral solvents such as aliphatic hydrocarbons, cycloalkanes, aromatic hydrocarbons and the like. For example, the solvent may be a fatty alcohol, glycol ethers, ethyl acetate, methyl ethyl ketone, methyl isobutyl ketone, ethylene glycol monomethyl ether ester, γ-butyrolactone, ethyl 3-ethoxypropionate, butyl carbitol, butyl carbitol acetate, propylene glycol monomethyl ether, cyclohexane, xylene, isopropanol, or the like; and preferably cyclohexanone, propylene glycol monomethyl ether acetate, cyclohexane, xylene, butyl carbitol, butyl carbitol acetate, ethyl 3-ethoxypropionate, γ-butyrolactone, or the like.

The initiator is an optional component used for producing free radicals or ions that can initiate polymerization, thereby curing the above curable resin. For example, the initiator can be a photoinitiator or thermal initiator, preferably a photoinitiator. This is because the requirement that the initiation temperature of the thermal initiator should be lower than the heat resistant temperature of the light guide plate must be taken into account. Generally speaking, optional photoinitiators comprise: oxime ester photoinitiators, amine ketone photoinitiators, aromatic ketone photoinitiators, acetophenone-based photoinitiators, acylphosphine oxides, aromatic sulfonium salt photoinitiators, iodonium salt photoinitiators, ferrocenium photoinitiators, macromolecular photoinitiators and the like. For example, oxime ester photoinitiators may include 1-[4-(thiophenyl)phenyl]-octane-1,2-dione 2-(O-benzoyl oxime) and the like; acetophenone-based photoinitiators may include sulfur-containing acetophenone-based photoinitiators containing morpholin tertiary amino and thioether groups, which have a synergistic effect when used in combination with thioxanthone; aromatic ketone photoinitiators may include: 2-phenylbenzyl-2-dimethylamine-1-(4-morpholin benzyl phenyl)butanone, benzophenone and derivatives thereof, methyl o-benzoyl benzoate, thioxanthone and the like; aromatic sulfonium salt photoinitiators may include UVI-6976, UVI-6992 and the like; iodonium salt photoinitiators may include triphenylsulfonium salts, diaryl iodonium salts and the like; ferrocenium photoinitiators may include η6-cumene ferrocene oxidizing salt, η6-pyrene ferrocene oxidizing salt and the like; macromolecular photoinitiators may include cationic onium salts containing a long chain alkyl group (or alkoxyl group, ester group), cations containing a polyurethane group, cations containing a polyaromatic ring and the like.

The pigment is an optional component used for reducing the color shift that may be produced by a backlight module. Since scattering patterns, light guide plates and the like have different absorption capacities towards light at different wavelengths, the light emitted from the light guide plate may produce a certain color shift. Therefore, the color of light can be balanced by adding a pigment to absorb light of other wavebands. Specifically, pigments include a mixture of two or more of red pigments, green pigments, blue pigments, violet pigments, and black pigments, and the desired color can be obtained by their combinations. More specifically, the model numbers for red pigments can be P.R.122, P.R.123, P.R.177, P.R.179, P.R.190, P.R.202, P.R.210, P.R.224, P.R.254, P.R.255, P.R.264, P.R.270, P.R.272, P.R.122, etc; the model numbers for green pigments can be P.G.37, P.G.36, P.G.7, etc; the model numbers for blue pigments can be P.B.15, P.B.15:3, P.B.15:6, P.B.15:4, P.B.1, P.B.2, P.B.22, P.B.16, P.B.60, P.B.66, etc; the model numbers for purple pigments can be P.V.32, P.V.36, P.V.38, P.V.39, P.V.23, P.V.9, P.V.1 and the like; and the model numbers for black pigments can be C.I.1, C.I.7 and the like.

The additive is an optional component used for improving the performance of the light guide ink in various aspects, which, for example, may comprise one or more of surfactants, leveling agents, wetting agents, adhesion promoters, antioxidants, ultraviolet absorbers, anti-flocculation agents, defoamers, stabilizers and the like.

The above functional material can improve the function of the environmental friendliness of the light guide ink by adding it to the light guide ink.

The functional material of the various Examples was prepared using the above preparation method according to the parameters in the following table.

Afterwards, a light guide ink was prepared from the functional material obtained further according to the parameters in the following table. There was no need to employ a specific adding sequence and a specific mixing method as long as the various components can be mixed uniformly.

Subsequently, the infrared emissivity of the light guide ink was measured according to the GB/T 7287-2008 standard, and the amount of negative ions produced thereby was measured using an air anion analyzer (for example, Japan KEC Corporation's KEC-900 type), and finally the transmissivity thereof was measured using a spectrophotometer (e.g., a UV-visible spectrophotometer UV2550 from Shimadzu Corporation, Japan). The results were shown in the following table.

In the light guide ink of the various Examples, polyurethane acrylate was used as the curable resin; silicon oxide having an average particle diameter of 200 nm was used as the scattering particle; 1-[4-(thiophenyl)phenyl]-1,2-octanedione 2-(O-benzoyloxime) was used as the initiator; propylene glycol monomethyl ether acetate was used as the solvent; a defoamer with the model number of BYK-057 was used as the additive; and P.B.15:6 was used as the pigment. Because the substances described above were all conventional in a light guide ink, the same substances were used to achieve comparability of the various Examples. Of course, those skilled in the art shall appreciate that it is also allowable to prepare a light guide ink using other conventional substances.

TABLE 1

Relevant parameters of the functional material and the light guide ink (content unit: by mass parts)

| | | Example | | | | | |
|---|---|---|---|---|---|---|---|
| item | | 1 | 2 | 3 | 4 | 5 | 6 |
| Inorganic powder | aluminum oxide amount | 0.002 | 0.01 | 0.014 | 0.014 | 0.019 | 0.029 |
| | titanium oxide Amount | 0.056 | 0.224 | 0.337 | 0.337 | 0.449 | 0.673 |
| | zirconium oxide amount | 0.021 | 0.084 | 0.126 | 0.126 | 0.168 | 0.252 |
| | silicon oxide amount | 0.019 | 0.04 | 0.06 | 0.06 | none | 0.12 |
| | boron oxide amount | none | 0.024 | 0.036 | 0.036 | 0.128 | 0.072 |
| | diiron trioxide amount | none | 0.012 | 0.018 | 0.018 | 0.024 | 0.036 |
| | sodium oxide amount | 0.002 | 0.006 | 0.009 | 0.009 | 0.012 | 0.018 |
| Total amount | | 0.1 | 0.4 | 0.6 | 0.6 | 0.8 | 1.2 |
| Type of dianhydride | | pyromellitic dianhydride | pyromellitic dianhydride | diphenyl ether dianhydride | pyromellitic dianhydride | diphenyl ether dianhydride | hexafluoro dianhydride |
| Type of diamine | | 3-amino benzylamine | hexahydro-m-xylylene diamine | m-xylylene diamine | 3-amino benzylamine | hexahydro-m-xylylene diamine | 3-amino benzylamine |
| Molar ratio of dianhydride to diamine | | 0.85 | 0.87 | 0.92 | 1 | 1.05 | 1.05 |
| Mass ratio of inorganic powder to reaction product | | 20 | 10 | 8 | 15 | 1 | 4 |
| Initiator for preparing the function material | | Azodiiso-butyronitrile | Azodiiso-butyronitrile | Azobisiso valeronitrile | Azobisiso valeronitrile | Azodiiso-butyronitrile | Azodiiso-butyronitrile |
| Heating temp. at the 1st stage (° C.) | | 35 | 40 | 70 | 60 | 50 | 55 |
| Heating time at the 1st stage (min) | | 40 | 40 | 20 | 25 | 30 | 25 |
| Heating temp. at the 2nd stage (° C.) | | 75 | 85 | 75 | 80 | 70 | 90 |
| Heating time at the 2nd stage (min) | | 40 | 25 | 30 | 35 | 40 | 30 |
| Amount of scattering particle | | 2 | 6 | 15 | 6 | 6 | 15 |
| Amount of curable resin | | 30 | 26 | 15 | 26 | 26 | 25 |
| Amount of pigment | | 0.15 | 0.15 | 0.04 | 0.15 | 0.15 | 0.04 |
| Amount of solvent | | 64.24 | 63.94 | 69.06 | 63.74 | 63.54 | 58.46 |
| Amount of initiator | | 3.5 | 3.5 | 0 | 3.5 | 3.5 | 0 |
| Amount of additive | | 0.01 | 0.01 | 0.3 | 0.01 | 0.01 | 0.3 |

TABLE 1-continued

Relevant parameters of the functional material and the light guide ink (content unit: by mass parts)

| Performance | Transmissivity (%) | 98 | 97 | 96.6 | 96.2 | 96 | 95.9 |
|---|---|---|---|---|---|---|---|
| | Infrared emissivity (%) | 50 | 62 | 83 | 90 | 91 | 92 |
| | Anion (/cm³) | 120 | 470 | 700 | 920 | 1150 | 1500 |

| | | Example | | | | |
|---|---|---|---|---|---|---|
| | item | 7 | 8 | 9 | 10 | 11 |
| Inorganic powder | aluminum oxide amount | 0.024 | 0.829 | 0.043 | 0.033 | 0.938 |
| | titanium oxide Amount | 0.561 | 0.673 | none | 0.785 | 0.898 |
| | zirconium oxide amount | 0.21 | 0.252 | 0.378 | 0.294 | 0.336 |
| | silicon oxide amount | 0.115 | 0.12 | 1.19 | 0.14 | 0.16 |
| | boron oxide amount | 0.06 | 0.072 | 0.108 | 0.084 | 0.096 |
| | diiron trioxide amount | 0.03 | 0.036 | 0.054 | 0.042 | 0.048 |
| | sodium oxide amount | none | 0.018 | 0.027 | 0.022 | 0.024 |
| | Total amount | 1 | 2 | 1.8 | 1.4 | 2.5 |
| | Type of dianhydride | hexafluoro dianhydride | diphenyl ether dianhydride | hexafluoro dianhydride | hexafluoro dianhydride | hexafluoro dianhydride |
| | Type of diamine | m-xylylene diamine | 2,7-diamino fluorene | m-xylylene diamine | 2,7-diamino fluorene | m-xylylene diamine |
| | Molar ratio of dianhydride to diamine | 1 | 0.9 | 0.9 | 0.85 | 0.92 |
| | Mass ratio of inorganic powder to reaction product | 20 | 1 | 7.5 | 16 | 16 |
| | Initiator for preparing the function material | Dimethyl azobis isobutyrate | Azodiiso-butyronitrile | Azobisiso valeronitrile | Azobisiso valeronitrile | Dimethyl azobis isobutyrate |
| | Heating temp. at the 1st stage (° C.) | 55 | 65 | 70 | 35 | 30 |
| | Heating time at the 1st stage (min) | 30 | 35 | 35 | 35 | 20 |
| | Heating temp. at the 2nd stage (° C.) | 90 | 100 | 95 | 70 | 80 |
| | Heating time at the 2nd stage (min) | 20 | 20 | 25 | 35 | 40 |
| | Amount of scattering particle | 15 | 20 | 22 | 20 | 25 |
| | Amount of curable resin | 26 | 32 | 38 | 36 | 45 |
| | Amount of pigment | 0.15 | 0.15 | 0.04 | 0.15 | 0.04 |
| | Amount of solvent | 54.34 | 43.14 | 37.86 | 38.94 | 27.16 |
| | Amount of initiator | 3.5 | 2.7 | 0 | 3.5 | 0 |
| | Amount of additive | 0.01 | 0.01 | 0.3 | 0.01 | 0.3 |
| Performance | Transmissivity (%) | 95.6 | 95.2 | 95 | 94.6 | 93.9 |
| | Infrared emissivity (%) | 93 | 94 | 95 | 96 | 99 |
| | Anion (/cm³) | 1590 | 1800 | 2000 | 2200 | 2700 |

It can be seen that the light guide ink of various Examples had high infrared emissivity and anion concentration as well as high transmissivity, which suggests that the properties of the light guide ink were not affected. Meanwhile, the light guide ink can produce far-infrared light and negative ions, thereby improving the environment.

The inorganic powder in the functional material of the present embodiment had a modified layer capable of allowing the inorganic powder to be well incorporated into the light guide ink and improving the inorganic powder's capacity to emit far-infrared light and negative ions.

The present embodiment further provided a light guide plate comprising a light-exiting surface and a back surface opposite to the light-exiting surface, wherein the back surface was provided with a scattering pattern formed by curing the above light guide ink.

The scattering pattern might be in the form of a scattering network or the like, and was formed by applying a light guide ink onto the back surface of a light guide plate by means of screen printing and the like and then curing it. According to the initiator types in the scattering pattern, the curing might be UV curing or thermal curing. The thermal curing might have a curing temperature of 40° C. to 80° C. for a period of 0.5 to 2 h. Since the specific method for forming a scattering pattern from a light guide ink is known, not further details will be given herein.

The light guide plate of the present embodiment had a scattering pattern generated from the above light guide ink, and therefore could constantly emit far-infrared light and negative ions during use and was environmentally friendly.

It should be appreciated that the above embodiments are merely exemplary embodiments to illustrate the principles of the present invention, but the present invention is not limited thereto. Those of ordinary skill in the art, without departing from the spirit and essence of the present invention, may make various changes and improvements. Such changes and improvements are deemed within the scope of the invention.

The present application claims the priority of the Chinese Patent Application No. 201410367169.0 filed on Jul. 29, 2014, which is incorporated herein by reference as part of the disclosure of the present application.

What is claimed is:

1. A light guide ink, comprising:
    a curable resin;
    a scattering particle;
    a solvent; and
    a functional material comprising an inorganic powder whose surface has a modified layer, wherein
    the inorganic powder comprises any one or more of aluminum oxide, magnesium oxide, zinc oxide, zirconium oxide, silicon dioxide, titanium dioxide, boron oxide, diiron trioxide, calcium oxide, potassium oxide, sodium oxide and lithium oxide; and
    the modified layer is generated by a reaction of a dianhydride and a diamine;

wherein the light guide ink further comprises a pigment, an additive and an initiator; and without calculating the mass of the modified layer in the functional material, the mass percentages of the components in the light guide ink are:
the scattering particle: 2 to 25%;
the curable resin: 10 to 50%;
the pigment: 0.01 to 0.5%;
the solvent: 20 to 75%;
the initiator: 0 to 8.5%; and
the inorganic powder: 0.1 to 2.5%.

2. The light guide ink according to claim 1, wherein, without calculating the mass of the modified layer in the functional material, the mass percentage of the inorganic powder in the functional material is 0.1 to 2% based on the light guide ink.

3. The light guide ink according to claim 2, wherein, without calculating the mass of the modified layer in the functional material, the mass percentage of the inorganic powder in the functional material is 0.1 to 1.8% based on the light guide ink.

4. The light guide ink according to claim 1, wherein the molar ratio of the dianhydride to the diamine for generating the modified layer is from 0.85:1 to 1.05:1.

5. The light guide ink according to claim 4, wherein the molar ratio of the dianhydride to the diamine for generating the modified layer is from 0.92:1 to 1.05:1.

6. The light guide ink according to claim 1, wherein
the dianhydride for generating the modified layer comprises at least one phenyl group; and
the diamine for generating the modified layer comprises at least one phenyl ring or at least one non-phenyl six-membered carbocyclic ring.

7. The light guide ink according to claim 6, wherein
the dianhydride for generating the modified layer is selected from any one of pyromellitic dianhydride, benzophenone dianhydride, biphenyl dianhydride, diphenyl ether dianhydride, and 4,4'-(hexafluoroisopropylidene)diphthalic anhydride; and
the diamine for generating the modified layer is selected from any one of 3-amino benzylamine, 2,2'-difluoro-4,4'-(9-fluorenylidene) dianiline, 2,2-bis(3-amino-4-hydroxyphenyl) hexafluoropropane, hexahydro-m-xylylene diamine, 1,4-bis(aminomethyl) cyclohexane, 2,2-bis[4-(4-aminophenoxy)phenyl]hexafluoropropane, 2,2-bis(3-amino-4-methylphenyl) hexafluoropropane, 2,2-bis(3-aminophenyl) hexafluoropropane, 2,2-bis(4-aminophenyl) hexafluoropropane, 2,7-diamino fluorene, m-xylylene diamine, and 4,4'-methylene bis (2-ethyl-6-methylaniline).

8. The light guide ink according to claim 1, wherein the inorganic powder has a particle diameter of 1 to 5000 nm.

* * * * *